(12) United States Patent
Noguchi et al.

(10) Patent No.: US 11,717,264 B2
(45) Date of Patent: Aug. 8, 2023

(54) ULTRASOUND PROBE

(71) Applicant: FUJIFILM Corporation, Tokyo (JP)

(72) Inventors: Shinsuke Noguchi, Kanagawa (JP); Tomoki Inoue, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 190 days.

(21) Appl. No.: 17/216,887

(22) Filed: Mar. 30, 2021

(65) Prior Publication Data

US 2021/0212664 A1   Jul. 15, 2021

Related U.S. Application Data

(63) Continuation of application No. PCT/JP2019/036717, filed on Sep. 19, 2019.

(30) Foreign Application Priority Data

Oct. 11, 2018  (JP) .................................. 2018-192673

(51) Int. Cl.
*A61B 8/00* (2006.01)
*A61B 90/90* (2016.01)

(52) U.S. Cl.
CPC .......... *A61B 8/4472* (2013.01); *A61B 8/4488* (2013.01); *A61B 8/56* (2013.01); *A61B 90/90* (2016.02); *A61B 2560/0214* (2013.01)

(58) Field of Classification Search
CPC ....... A61B 8/4472; A61B 8/4488; A61B 8/56; A61B 90/90; A61B 2560/0214;

(Continued)

(56) References Cited

U.S. PATENT DOCUMENTS

2001/0004397 A1* 6/2001 Kita ...................... G04G 21/00
                                                                 381/334
2007/0102502 A1  5/2007 Nguyen
(Continued)

FOREIGN PATENT DOCUMENTS

CN   207892368 U   9/2018
JP   H09-206274 A  8/1997
(Continued)

OTHER PUBLICATIONS

International Search Report issued in PCT/JP2019/036717; dated Nov. 5, 2019.

(Continued)

*Primary Examiner* — Yi-Shan Yang
*Assistant Examiner* — Alexei Bykhovski
(74) *Attorney, Agent, or Firm* — Studebaker & Brackett PC

(57) ABSTRACT

An ultrasound probe 11 includes a housing 12 having a transducer array accommodation portion 14 and a battery storage portion 13B, a transducer array accommodated in the transducer array accommodation portion 14, and a battery 21 stored in the battery storage portion 13B. The housing 12 has an attachable and detachable battery cover 17 that covers the battery storage portion 13B, a nameplate 22 is disposed on an inside or an outside of the battery storage portion 13B with respect to the battery cover 17 in a visible manner, and a waterproof structure for restraining water from entering the nameplate 22 is provided.

3 Claims, 5 Drawing Sheets

(58) Field of Classification Search
CPC ....... A61B 8/4427; A61B 8/44; A61B 8/4438; A61B 90/94; Y02E 60/10
See application file for complete search history.

(56) References Cited

U.S. PATENT DOCUMENTS

| | | | | |
|---|---|---|---|---|
| 2009/0028286 | A1* | 1/2009 | Prestidge | G01B 5/012 33/559 |
| 2012/0078111 | A1* | 3/2012 | Tanabe | A61B 8/56 600/459 |
| 2014/0017466 | A1* | 1/2014 | Won | C09J 7/22 428/354 |
| 2016/0331344 | A1* | 11/2016 | Hadzic | A61B 8/085 |
| 2019/0145802 | A1* | 5/2019 | Kobata | G01D 7/00 73/1.88 |
| 2019/0168493 | A1* | 6/2019 | Takeda | B32B 27/308 |
| 2019/0372071 | A1* | 12/2019 | An | H01M 50/559 |

FOREIGN PATENT DOCUMENTS

| | | | | |
|---|---|---|---|---|
| JP | 2001007546 | * | 6/1999 | |
| JP | 2001-007546 | A | 1/2001 | |
| JP | 2006-026236 | A | 2/2006 | |
| JP | 2012-071041 | A | 4/2012 | |
| WO | 2005/091249 | A1 | 9/2005 | |
| WO | WO2005/091249 | * | 9/2005 | ............... G09B 9/00 |

OTHER PUBLICATIONS

International Preliminary Report on Patentability and Written Opinion issued in PCT/JP2019/036717; dated Apr. 8, 2021.
The extended European search report issued by the European Patent Office dated Nov. 18, 2021, which corresponds to European Patent Application No. 19871350.5-1126 and is related to U.S. Appl. No. 17/216,887.

* cited by examiner

ULTRASOUND PROBE

CROSS-REFERENCE TO RELATED APPLICATIONS

This application is a Continuation of PCT International Application No. PCT/JP2019/036717 filed on Sep. 19, 2019, which claims priority under 35 U.S.C. § 119(a) to Japanese Patent Application No. 2018-192673 filed on Oct. 11, 2018. The above application is hereby expressly incorporated by reference, in its entirety, into the present application.

BACKGROUND OF THE INVENTION

1. Field of the Invention

The present invention relates to an ultrasound probe, and in particular, to an ultrasound probe having a nameplate.

2. Description of the Related Art

Hitherto, in a medical field, an ultrasound diagnostic apparatus using an ultrasound image has come into practical use. In general, this kind of ultrasound diagnostic apparatus has an ultrasound probe that incorporates a transducer array, and an apparatus body connected to the ultrasound probe. The ultrasound probe transmits ultrasonic waves toward a subject and receives ultrasound echoes from the subject, and the apparatus body electrically processes reception signals to generate an ultrasound image.

Such an ultrasound diagnostic apparatus is medical equipment, and thus, necessary items, such as a name and an address of a manufacturer/dealer, a name of equipment, and a serial number, are required to be described on an equipment body under the provision of Article 63 of the Pharmaceutical Affairs Law. Typically, the description is performed by fixing a label, a plate, or the like, called a "nameplate", on which the necessary items are printed, to the equipment body.

For example, in an ultrasound probe disclosed in JP2006-026236A, a label as a nameplate is adhered to a recess portion formed in a surface of a housing of the ultrasound probe.

SUMMARY OF THE INVENTION

Note that the ultrasound probe is used in a state of being brought into contact with the subject, and thus, in general, there is a need to perform cleaning, sterilization, disinfection, and the like using a chemical, such as isopropyl alcohol. For this reason, like the ultrasound probe disclosed in JP2006-026236A, in a case where the label as the nameplate is adhered to the surface of the housing of the ultrasound probe, there is a problem that the description of the label is damaged by repeating cleaning, sterilization, disinfection, and the like.

In a case of a wired connection type ultrasound probe that is connected to a diagnostic apparatus body through a connection cable, it is possible to restrain damage to the description of the nameplate accompanied by cleaning, sterilization, disinfection, and the like of the ultrasound probe by adhering the nameplate to a connector portion of the connection cable for connection to the diagnostic apparatus body. Meanwhile, in a case of a wireless connection type ultrasound probe that does not use a connection cable, the nameplate should be adhered to the ultrasound probe itself, and it is desirable to protect the description of the nameplate from the chemical.

The invention has been accomplished to solve such a problem in the related art, and an object of the invention is to provide an ultrasound probe that restrains damage to description of a nameplate.

To achieve the above-described object, the invention provides an ultrasound probe comprising a housing having a transducer array accommodation portion and a battery storage portion, a transducer array accommodated in the transducer array accommodation portion, and a battery stored in the battery storage portion. The housing has an attachable and detachable battery cover that covers the battery storage portion, a nameplate is disposed on an inside or an outside of the battery storage portion with respect to the battery cover in a visible manner, and a waterproof structure for restraining water from entering the nameplate is provided.

It is preferable that the nameplate is disposed on an outer surface of the battery cover toward the outside of the battery storage portion, and the waterproof structure has a transparent cover that covers the nameplate.

The transparent cover may be adhered to the outer surface of the battery cover by a waterproof double-sided tape in a vicinity of the nameplate.

Non-transparent printing may be performed on a portion of the transparent cover in the vicinity of the nameplate.

Alternatively, it is preferable that the battery cover has a transparent portion, the nameplate is disposed on the inside of the battery storage portion with respect to the transparent portion of the battery cover, and the waterproof structure is constituted by the battery cover.

In this case, the nameplate may be adhered to an inner surface of the transparent portion of the battery cover toward the inside of the battery storage portion.

The nameplate may be disposed in an internal structure member of the battery storage portion facing the transparent portion of the battery cover.

It is preferable that the battery cover has the transparent portion at a center, and the battery cover in a portion positioned in a vicinity of the transparent portion is non-transparent.

According to the invention, the ultrasound probe comprises the housing having the transducer array accommodation portion and the battery storage portion, the transducer array accommodated in the transducer array accommodation portion, and the battery stored in the battery storage portion, the housing has the attachable and detachable battery cover that covers the battery storage portion, the nameplate is disposed on the inside or the outside of the battery storage portion with respect to the battery cover in a visible manner, and a waterproof structure for restraining water from entering the nameplate is provided. Thus, it is possible to restrain damage to the description of the nameplate.

DESCRIPTION OF THE PREFERRED EMBODIMENTS

Hereinafter, embodiments of the invention will be described referring to the accompanying drawings.

Embodiment 1

Figure 1:
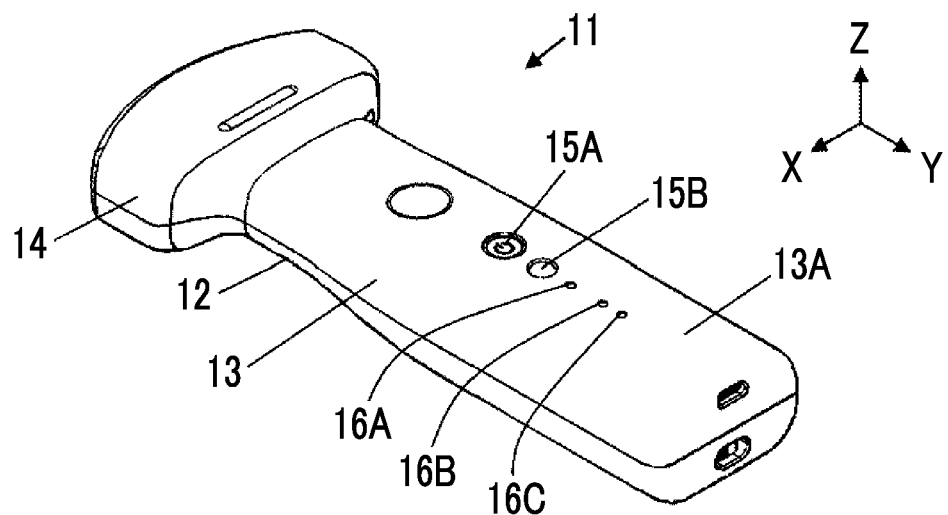
FIG. 1 is a perspective view of an ultrasound probe according to Embodiment 1 of the invention viewed from above.

FIG. 1 shows an ultrasound probe 11 according to an embodiment of the invention. As shown in FIG. 1, the ultrasound probe 11 comprises a housing 12, and the housing 12 has a grip portion 13 that extends in a determined direction and has a wide and flat cross-sectional shape, and a transducer array accommodation portion 14 that is connected to one end portion of the grip portion 13. The transducer array accommodation portion 14 is formed to be wider and thicker than the grip portion 13. A probe operating surface 13A is defined in a surface of the other end portion of the grip portion 13, and operation switches 15A and 15B of the ultrasound probe 11 and indicators 16A, 16B, and 16C are disposed in the probe operating surface 13A.

Hereinafter, for description, a direction from the transducer array accommodation portion 14 toward the grip portion 13 along a direction in which the grip portion 13 extends is referred to as a +Y direction, a width direction of the grip portion 13 perpendicular to the Y direction is referred to as an X direction, and a thickness direction of the ultrasound probe 11 perpendicular to the Y direction and the X direction is referred to as a Z direction. The operating surface 13A of the grip portion 13 is defined in a surface on a +Z direction side of the grip portion 13.

Figure 2:
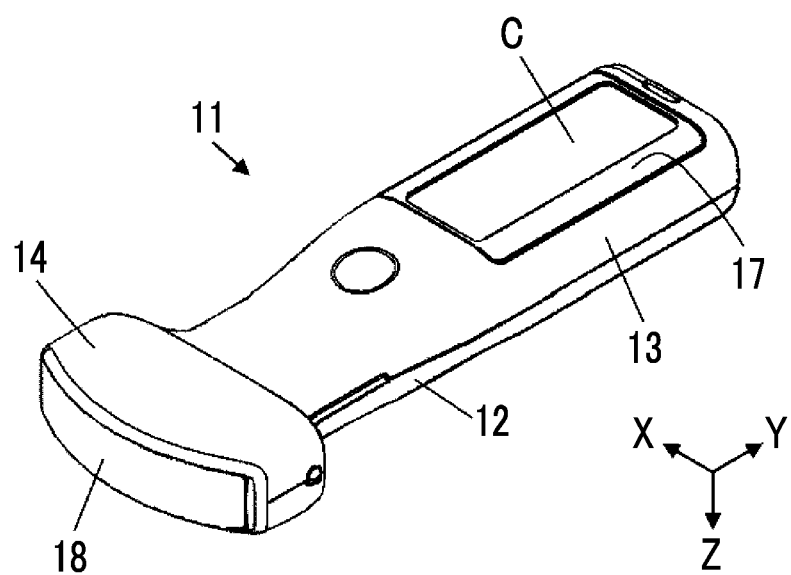
FIG. 2 is a perspective view of the ultrasound probe according to Embodiment 1 of the invention viewed from below.

As shown in FIG. 2, an attachable and detachable battery cover 17 is disposed on a -Z direction side of the other end portion of the grip portion 13, and a transparent cover C is disposed on the battery cover 17. Here, the transparent cover C is made of transmissive resin or the like, and for example, in a case where the user views the transparent cover C from the -Z direction, the user can view a +Z direction side of the transparent cover C through a surface on the -Z direction side of the transparent cover C.

An acoustic lens 18 is disposed in an end portion of the transducer array accommodation portion 14 in a -Y direction.

Figure 3:
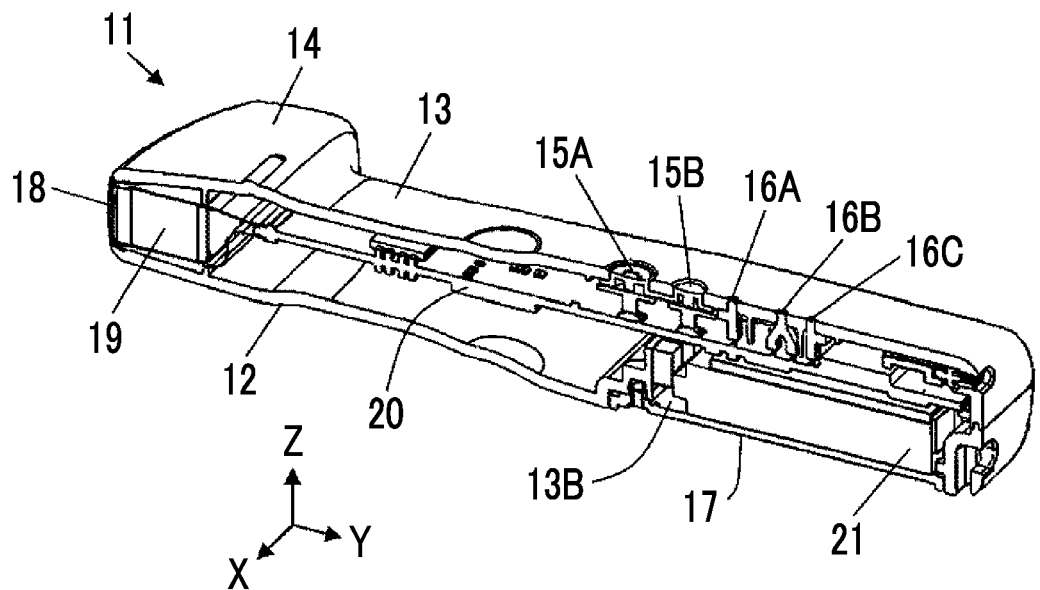
FIG. 3 is a cross-sectional view of the ultrasound probe according to Embodiment 1 of the invention.

FIG. 3 is a sectional view of the ultrasound probe 11 along a YZ plane passing through the operation switches 15A and 15B and the indicators 16A to 16C. As shown in FIG. 3, the transducer array 19 is accommodated in the transducer array accommodation portion 14, and a circuit substrate 20 is disposed in the housing 12 from the transducer array accommodation portion 14 to an end portion of the grip portion 13 in the +Y direction. Here, the transducer array 19 has a plurality of transducers arranged along the XY plane, and is connected to the circuit substrate 20 through a plurality of wirings.

A recessed battery storage portion 13B that is positioned on the -Z direction side with respect to the circuit substrate 20 and is covered with the battery cover 17 from the -Z direction side is formed in the end portion of the grip portion 13 in the +Y direction. A battery 21 is stored in the battery storage portion 13B, and the battery 21 is connected to the circuit substrate 20. The battery 21 is replaceable by detaching the battery cover 17.

The operation switches 15A and 15B and the indicators 16A to 16C are connected to the circuit substrate 20. The operation switches 15A and 15B are operated by the user, for example, for supply of power of the ultrasound probe 11, cutoff of power of the ultrasound probe 11, and an instruction of the operation of the ultrasound probe 11. The indicators 16A to 16C are constituted of, for example, a light emitting diode (LED), and emit light in response to a signal from the circuit substrate 20 to perform various kinds of notification, such as a supply state of power, a remaining capacity of the battery 21, and an operation state of the ultrasound probe 11.

Here, the ultrasound probe 11 is used to transmit and receive ultrasonic waves to and from a subject with the transducer array 19 to capture an ultrasound image representing a tomographic plane of the subject, and is connected to a diagnostic apparatus body that generates and displays the ultrasound image based on signals acquired by the ultrasound probe 11 as described below.

Figure 4:
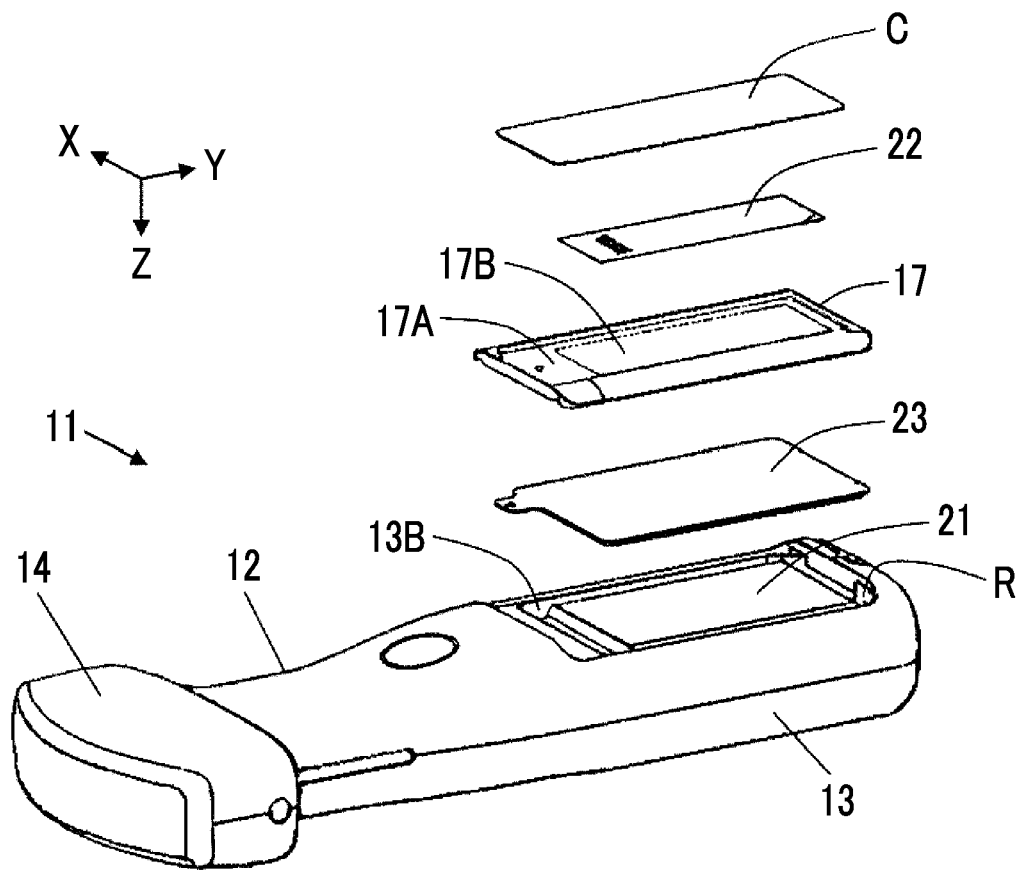
FIG. 4 is an exploded view of the periphery of a battery cover of the ultrasound probe according to Embodiment 1 of the invention.

As shown in FIG. 4, the ultrasound probe 11 has a nameplate 22 that is disposed between the battery cover 17 and the transparent cover C, and a waterproof member 23 that is disposed between the battery cover 17 and the battery 21. Here, the nameplate 22 is a plate on which items, such as a name and an address of a manufacturer/dealer of the ultrasound probe 11, a name of equipment, and a serial number, are described. Such items are required to be described in medical equipment under the provision of Article 63 of the Pharmaceutical Affairs Law. The nameplate 22 is not limited to a plate as long as the necessary items, such as the name and the address of the manufacturer/dealer of the ultrasound probe 11, the name of the equipment, and the serial number, are described, and may be a sheet-shaped label or the like.

In a surface on the -Z direction side of the battery cover 17, a first recess portion 17A that is recessed in the +Z direction and has a flat bottom portion along the XY plane, and a second recess portion 17B that is further recessed in the +Z direction than the first recess portion 17A and has a flat bottom portion along the XY plane are formed. Here, the second recess portion 17B is formed inside the first recess portion 17A and is surrounded by the flat bottom portion of the first recess portion 17A.

The nameplate 22 is disposed in the second recess portion 17B of the battery cover 17, and the transparent cover C is disposed upward of the nameplate 22 and in the first recess portion 17A of the battery cover 17. The battery cover 17 and the transparent cover C are adhered by a waterproof double-sided tape (not shown) surrounding the vicinity of the nameplate 22. For this reason, a waterproof structure for the nameplate 22 is constituted by the transparent cover C and the waterproof double-sided tape, and a liquid, such as water or chemical, is restrained from entering the nameplate 22 from the outside. For example, a waterproof structure is also constituted by bonding a peripheral portion of the transparent cover C surrounding the nameplate 22 to the bottom portion of the first recess portion 17A of the battery cover 17 using a waterproof adhesive, instead of the double-sided tape.

The waterproof member 23 has a waterproof rim (not shown) that protrudes from a surface on the +Z direction side. The waterproof rim is a ring-shaped projection portion that is formed of an elastic material along an inner wall surface of the battery storage portion 13B to surround the vicinity of the battery 21. In a case where the battery cover 17 is attached to the grip portion 13 in a state in which the waterproof member 23 is disposed on the battery 21, the waterproof rim is inserted between the battery 21 and the inner wall surface of the battery storage portion 13B, the waterproof rim is pressed and closely attached to the inner wall surface of the battery storage portion 13B, and a liquid, such as water or chemical, is restrained from entering the battery 21 from the outside.

Figure 5:
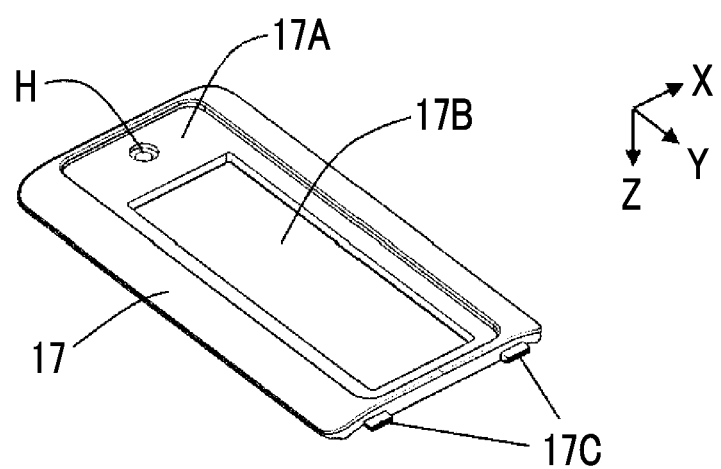
FIG. 5 is a perspective view of the battery cover in Embodiment 1 of the invention.

As shown in FIG. 5, two hook portions 17C protrude in an end portion of the battery cover 17 in the +Y direction, and a through-hole H that passes through the battery cover 17 is formed in the flat bottom portion of the first recess portion 17A of the battery cover 17. As shown in FIG. 4, two recess portions R into which the two hook portions 17C of the battery cover 17 are formed in an inner wall surface on the +Y direction side of the battery storage portion 13B of the grip portion 13, and a screw hole (not shown) corresponding to the through-hole H of the battery cover 17 is formed near an end portion on the −Y direction side of the battery storage portion 13B. The battery cover 17 is fixed to the grip portion 13 by inserting a screw (not shown) into the through-hole H of the battery cover 17 and screwing the screw into the screw hole of the grip portion 13 in a state in which the two hook portions 17C of the battery cover 17 are inserted into the two recess portions R of the grip portion.

Here, in general, the ultrasound probe is used in a state of being brought into contact with the subject, and thus, there is a need to perform cleaning, sterilization, disinfection, and the like using a chemical, such as isopropyl alcohol. With the ultrasound probe 11 according to Embodiment 1 of the invention, the nameplate 22 is covered with the transparent cover C in a state of being disposed in the second recess portion 17B of the battery cover 17, and the waterproof structure for the nameplate 22 is constituted by the transparent cover C and the waterproof double-sided tape (not shown). Thus, even though cleaning, sterilization, disinfection, and the like of the ultrasound probe 11 are repeatedly performed, the chemical, such as isopropyl alcohol, is restrained from entering the nameplate 22 from the outside, and the description of the nameplate 22 is restrained from being damaged.

Figure 6:
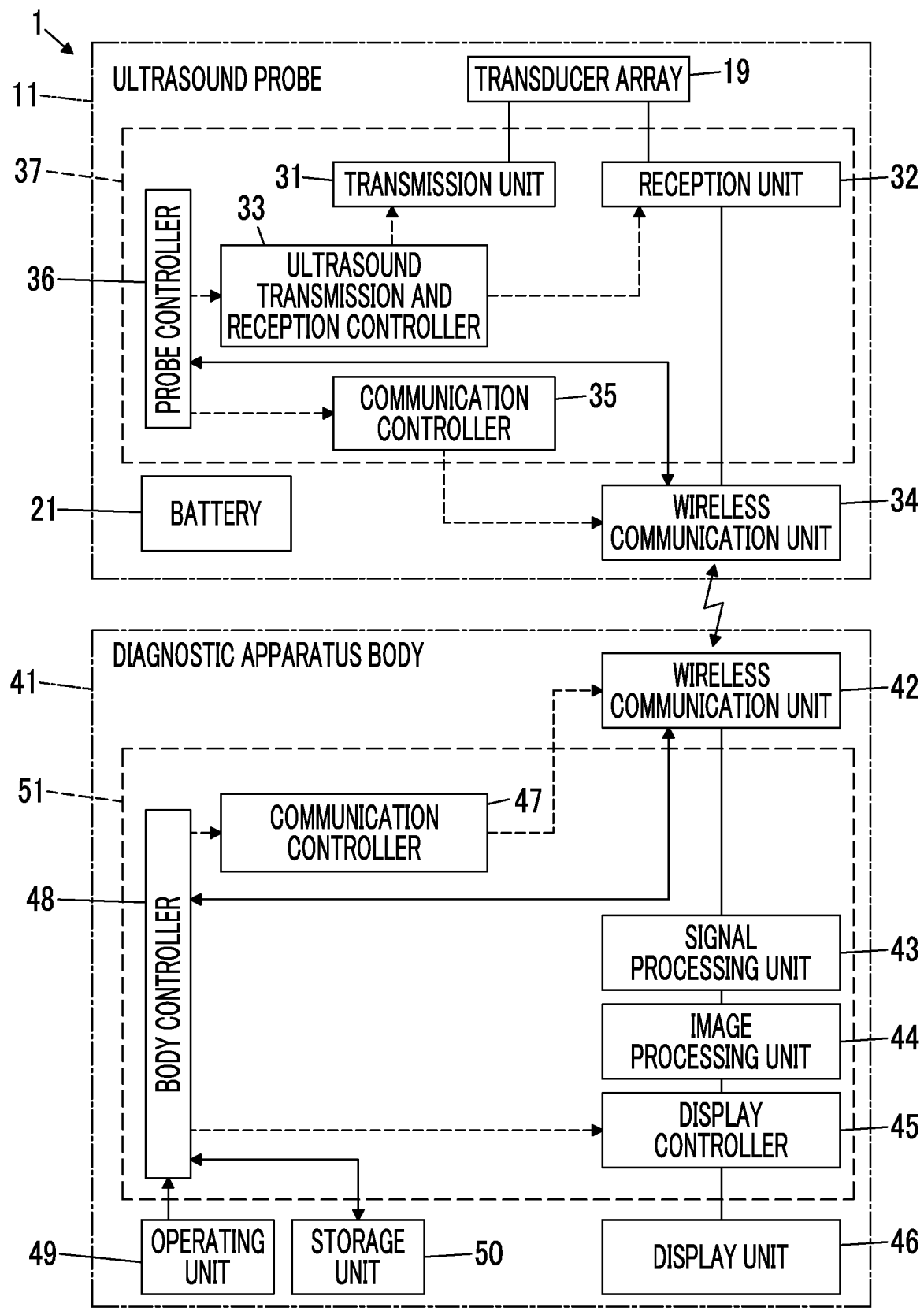
FIG. 6 is a block diagram showing the configuration of an ultrasound diagnostic apparatus comprising the ultrasound probe according to Embodiment 1 of the invention.

Next, an ultrasound diagnostic apparatus 1 comprising the ultrasound probe 11 according to Embodiment 1 of the invention will be described. FIG. 6 shows the configuration of the ultrasound diagnostic apparatus 1. As shown in FIG. 6, the ultrasound diagnostic apparatus 1 comprises the ultrasound probe 11 according to Embodiment 1 of the invention and a diagnostic apparatus body 41, and the ultrasound probe 11 and the diagnostic apparatus body 41 are connected through wireless communication.

The ultrasound probe 11 comprises the transducer array 19, and a transmission unit 31 and a reception unit 32 are connected to the transducer array 19. An ultrasound transmission and reception controller 33 is connected to the transmission unit 31 and the reception unit 32. A wireless communication unit 34 is connected to the reception unit 32, and a communication controller 35 is connected to the wireless communication unit 34. A probe controller 36 is connected to the ultrasound transmission and reception controller 33, the wireless communication unit 34, and the communication controller 35. Here, the wireless communication unit 34 and the probe controller 36 are connected in such a manner that information can be transferred in two directions. The ultrasound probe 11 incorporates the battery 21.

The transmission unit 31, the reception unit 32, the ultrasound transmission and reception controller 33, the communication controller 35, and the probe controller 36 constitute an ultrasound probe-side processor 37.

The diagnostic apparatus body 41 comprises a wireless communication unit 42, and a signal processing unit 43, an image processing unit 44, a display controller 45, and a display unit 46 are sequentially connected to the wireless communication unit 42. A communication controller 47 is connected to the wireless communication unit 42, and a body controller 48 is connected to the wireless communication unit 42, the communication controller 47, and the display controller 45. An operating unit 49 and a storage unit 50 are connected to the body controller 48. Here, the wireless communication unit 42 and the body controller 48, and the body controller 48 and the storage unit 50 are connected in such a manner that information can be transferred in two directions.

The signal processing unit 43, the image processing unit 44, the display controller 45, the communication controller 47, and the body controller 48 constitute a diagnostic apparatus body-side processor 51.

The wireless communication unit 34 of the ultrasound probe 11 and the wireless communication unit 42 of the diagnostic apparatus body 41 are connected in such a manner that information can be transferred in two directions. With this, the ultrasound probe 11 and the diagnostic apparatus body 41 are connected through wireless communication.

The transducer array 19 of the ultrasound probe 11 shown in FIG. 5 has a plurality of transducers arranged in a one-dimensional or two-dimensional manner. The transducers transmit ultrasonic waves in compliance with drive signals supplied from the transmission unit 31, receive ultrasound echoes from the subject, and output reception signals. Each transducer is constituted by forming electrodes at both ends of a piezoelectric body consisting of, for example, piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

The ultrasound transmission and reception controller 33 of the ultrasound probe-side processor 37 performs control such that the transmission unit 31 and the reception unit 32 perform transmission of an ultrasonic beam and reception of ultrasound echoes based on an instruction from the probe controller 36, respectively.

The transmission unit 31 of the ultrasound probe-side processor 37 includes, for example, a plurality of pulse generators, and adjusts a delay amount of each drive signal based on a transmission delay pattern selected in response to a control signal from the ultrasound transmission and reception controller 33 such that ultrasonic waves transmitted from a plurality of transducers of the transducer array 19 form an ultrasonic beam, and supplies the drive signals to a plurality of transducers. In this way, in a case where a pulsed or continuous-wave voltage is applied to the electrodes of each of a plurality of transducers of the transducer array 19, the piezoelectric body expands and contracts to generate a pulsed or continuous-wave ultrasonic wave from each of the transducers. An ultrasonic beam is formed from a combined wave of the ultrasonic waves.

The transmitted ultrasonic beam is reflected by, for example, a target, such as a part of the subject, and propagates toward the transducer array 19 of the ultrasound probe 11. The ultrasound echo propagating toward the transducer array 19 is received by each transducer constituting the transducer array 19. In this case, each transducer constituting the transducer array 19 expands and contracts with reception of the propagating ultrasound echo to generate an electrical signal, and outputs the electrical signal to the reception unit 32.

Figure 7:
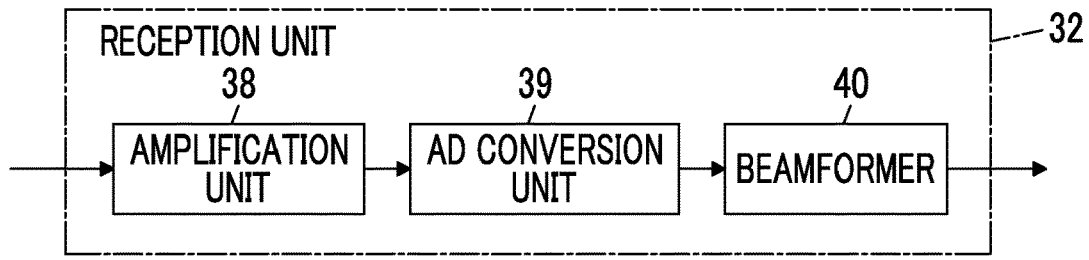
FIG. 7 is a block diagram showing the internal configuration of a reception unit in Embodiment 1 of the invention.

The reception unit 32 of the ultrasound probe-side processor 37 executes processing of the reception signals output from the transducer array 19 in compliance with a control signal from the ultrasound transmission and reception controller 33. As shown in FIG. 7, the reception unit 32 has a configuration in which an amplification unit 38, an analog-digital (AD) conversion unit 39, and a beamformer 40 are connected in series. The amplification unit 38 amplifies the reception signal input from each of the transducers constituting the transducer array 19 and transmits the amplified reception signal to the AD conversion unit 39. The AD conversion unit 39 converts the reception signal transmitted from the amplification unit 38 into digitized data and sends the digitized data to the beamformer 40. The beamformer 40 executes reception focus processing of giving a delay to each piece of data compliant with a set sound speed based on a reception delay pattern selected in response to a control signal from the ultrasound transmission and reception controller 33 and performing addition (phasing addition). With the reception focus processing, a sound ray signal in which a focus of the ultrasound echo is narrowed on a given scanning line is generated. The sound ray signal generated in this manner is sent to the wireless communication unit 34 of the ultrasound probe 11.

The wireless communication unit 34 of the ultrasound probe 11 includes an antenna that performs transmission and reception of radio waves, and performs wireless communication with the wireless communication unit 42 of the diagnostic apparatus body 41. In this case, the wireless communication unit 34 modulates a carrier based on the sound ray signal sent from the reception unit 32 to generate a transmission signal and transmits the generated transmission signal to the wireless communication unit 42 of the diagnostic apparatus body 41 in a wireless manner. As a modulation system of the carrier, for example, amplitude shift keying (ASK), phase shift keying (PSK), quadrature phase shift keying (QPSK), 16 quadrature amplitude modulation (16QAM), or the like is used.

The communication controller 35 of the ultrasound probe-side processor 37 performs control such that the wireless communication unit 34 of the ultrasound probe 11 transmits the sound ray signal with transmission field intensity set by the probe controller 36.

The probe controller 36 of the ultrasound probe-side processor 37 performs control of each unit of the ultrasound probe 11 based on a program or the like stored in advance.

The battery 21 of the ultrasound probe 11 is incorporated in the ultrasound probe 11, and supplies electric power to each circuit of the ultrasound probe 11.

The wireless communication unit 42 of the diagnostic apparatus body 41 includes an antenna that performs transmission and reception of radio waves, and performs wireless communication with the wireless communication unit 34 of the ultrasound probe 11. In this case, the wireless communication unit 42 of the diagnostic apparatus body 41 outputs a sound ray signal, for example, by receiving the transmission signal transmitted from the wireless communication unit 34 of the ultrasound probe 11 in a wireless manner through the antenna and demodulating the received transmission signal. The wireless communication unit 42 of the diagnostic apparatus body 41 sends the sound ray signal output in this manner to the signal processing unit 43.

The signal processing unit 43 of the diagnostic apparatus body-side processor 51 performs correction of attenuation of the sound ray signal sent from the wireless communication unit 42 due to a propagation distance depending on a depth of a reflection position of the ultrasonic wave, and then, executes envelope detection to generate a signal as tomographic image information regarding a tissue in the subject.

The image processing unit 44 of the diagnostic apparatus body-side processor 51 generates an ultrasound image signal by raster-converting the signal generated by the signal processing unit 43 into an image signal in compliance with a normal television signal scanning system and executing various kinds of necessary image processing, such as brightness correction, tone correction, sharpness correction, and color correction, on the image signal generated in this manner. The image processing unit 44 sends the ultrasound image signal generated in this manner to the display controller 45.

The display controller 45 of the diagnostic apparatus body-side processor 51 executes predetermined processing on the ultrasound image signal generated by the image processing unit 44 and displays an ultrasound image on the display unit 46 under the control of the body controller 48.

The display unit 46 of the diagnostic apparatus body 41 displays an image under the control of the display controller 45, and includes, for example, a display device, such as a liquid crystal display (LCD), an organic electroluminescence display (organic EL display).

The communication controller 47 of the diagnostic apparatus body-side processor 51 performs control such that the wireless communication unit 42 of the diagnostic apparatus body 41 receives the transmission signal from the wireless communication unit 34 of the ultrasound probe 11.

The body controller 48 of the diagnostic apparatus body-side processor 51 performs control of each unit of the diagnostic apparatus body 41 based on a program stored in advance in the storage unit 50 or the like and a user's operation through the operating unit 49.

The operating unit 49 of the diagnostic apparatus body 41 is provided for the user to perform an input operation, and can comprise a keyboard, a mouse, a trackball, a touch pad, a touch panel, and the like.

The storage unit 50 of the diagnostic apparatus body 41 stores an operation program and the like of the diagnostic apparatus body 41, and as the storage unit 50, a recording medium, such as a hard disc drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), or a universal serial bus memory (USB memory), a server, or the like can be used.

Here, in the ultrasound probe 11, each of the ultrasound probe-side processor 37 having the transmission unit 31, the reception unit 32, the ultrasound transmission and reception controller 33, the communication controller 35, and the probe controller 36 and the diagnostic apparatus body-side processor 51 having the signal processing unit 43, the image processing unit 44, the display controller 45, the communication controller 47, and the body controller 48 is constituted of a central processing unit (CPU) and a control program causing the CPU to execute various kinds of processing. However, the ultrasound probe-side processor 37 and the diagnostic apparatus body-side processor 51 may be constituted using a field programmable gate array (FPGA), a digital signal processor (DSP), an application specific integrated circuit (ASIC), or other integrated circuits (ICs) or may be constituted by combining the IC circuits.

The transmission unit 31, the reception unit 32, the ultrasound transmission and reception controller 33, the communication controller 35, and the probe controller 36 of the ultrasound probe-side processor 37 may be constituted to be partially or wholly integrated into one CPU or the like. The signal processing unit 43, the image processing unit 44, the display controller 45, the communication controller 47, and the body controller 48 of the diagnostic apparatus body-side processor 51 may be constituted to be partially or wholly integrated into one CPU or the like.

Non-transparent printing can be performed on a portion of the transparent cover C positioned in the vicinity of the nameplate 22. With this, it is possible to hide the screw (not shown) for fixing the battery cover 17 to the grip portion 13 of the housing 12 while disposing the nameplate 22 on the battery cover 17 in a state of being viewed from the user. Although non-transparent printing can performed on at least one of a surface on the +Z direction side or a surface on the −Z direction side of the transparent cover C, it is preferable that non-transparent printing is performed on the surface on the side on which the nameplate 22 is disposed, that is, on the +Z direction side since non-transparent printing is not brought into contact with the chemical or the like.

Instead of non-transparent printing on the transparent cover C, a non-transparent sheet-shaped member or the like may be adhered to the transparent cover C as long as the vicinity of the nameplate 22 can be hidden.

The ultrasound probe 11 provides a waterproof rim (not shown) formed in the waterproof member 23 on the surface on the +Z direction side of the battery cover 17 to fix the battery cover 17 to the grip portion 13, instead of having the waterproof member 23 that restrains a liquid, such as water or a chemical, entering the battery 21, whereby it is also possible to restrain a liquid, such as water or a chemical, from entering the battery storage portion 13B.

In Embodiment 1, the ultrasound probe 11 has the waterproof member 23 separately from the battery cover 17. Thus, even though the waterproof member 23 does not have flame retardance, the housing 12 and the battery cover 17 are formed of a material having flame retardance, whereby it is possible to improve the fire protection property of the ultrasound probe 11. Here, examples of the material having flame retardance include an insulating resin material having flame retardance, such as modified polyphenylene ether (m-PPE) or polycarbonate/acrylonitrile-butadiene-styrene alloy (PC/ABS alloy). In particular, a resin material having flame retardance of a flame retardant grade V-1, V-0, SVB, or 5VA defined in the UL94 standard is preferably used.

Although the grip portion 13 in Embodiment 1 has a wide and flat cross-sectional shape, the shape of the grip portion 13 is not particularly limited.

Although the ultrasound probe 11 is connected to the diagnostic apparatus body 41 in a wireless manner, the ultrasound probe 11 may be connected to the diagnostic apparatus body 41 in a wired manner.

Embodiment 2

In Embodiment 1, although the nameplate 22 is disposed outside the battery cover 17, that is, on the −Z direction side, the invention is not limited thereto as long as the user can view the nameplate 22 from the outside. An ultrasound probe according to Embodiment 2 comprises a battery cover 57 shown in FIG. 8 instead of the battery cover 17 in the ultrasound probe 11 of Embodiment 1 shown in FIGS. 1 to 4.

Figure 8:
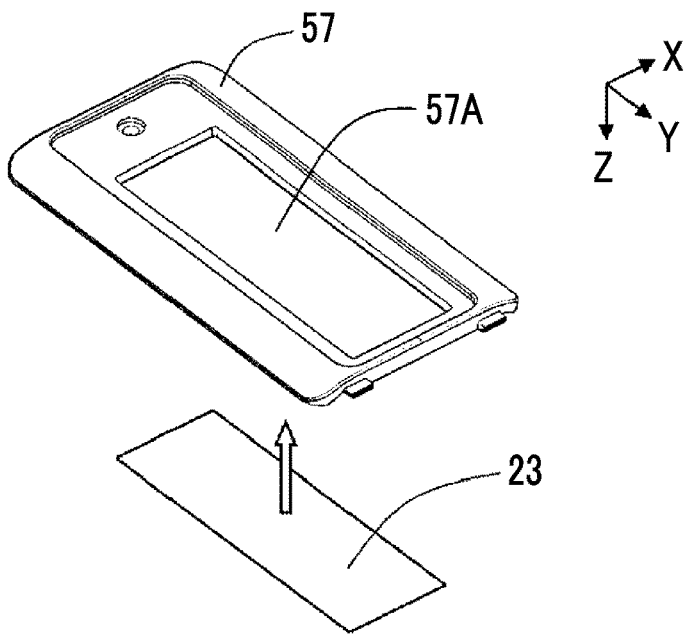
FIG. 8 is a diagram showing a manner in which a nameplate is attached to a rear surface of a battery cover in Embodiment 2 of the invention.

As shown in FIG. 8, the battery cover 57 has a transparent portion 57A in a center portion, and a portion other than the transparent portion 57A of the battery cover 57 is non-transparent. The transparent portion 57A has a size corresponding to the nameplate 22. Similarly to the transparent cover C in Embodiment 1, the transparent portion 57A is formed of transmissive resin or the like, and for example, in a case where the user views the transparent portion 57A from the −Z direction, the user can view the +Z direction side of the battery cover 57 through the transparent portion 57A.

The nameplate 22 is disposed on the +Z direction side of the transparent portion 57A such that the description of the nameplate 22 is directed in the −Z direction, and is adhered onto a surface on the +Z direction side of the transparent portion 57A of the battery cover 57. In this case, the nameplate 22 is adhered to the surface on the +Z direction side of the transparent portion 57A of the battery cover 57 from the +Z direction side such that an entire outer peripheral portion of the nameplate 22 is covered with a waterproof adhesive tape (not shown). A waterproof structure for the nameplate 22 is constituted by the battery cover 57 and the waterproof adhesive tape, and a liquid, such as water or a chemical, is restrained from entering the nameplate 22 from the outside. A waterproof structure for the nameplate 22 can also be constituted by bonding the outer peripheral portion of the nameplate 22 to the surface on the +Z direction side of the transparent portion 57A of the battery cover 57 using a waterproof adhesive or the like instead of the waterproof adhesive tape.

In such a manner, the nameplate 22 is disposed on the +Z direction side of the transparent portion 57A, whereby the user can view the description of the nameplate 22 through the transparent portion 57A. A liquid, such as water or a chemical, is restrained from entering the nameplate 22, and thus, the description of the nameplate 22 is restrained from being damaged.

Figure 9:
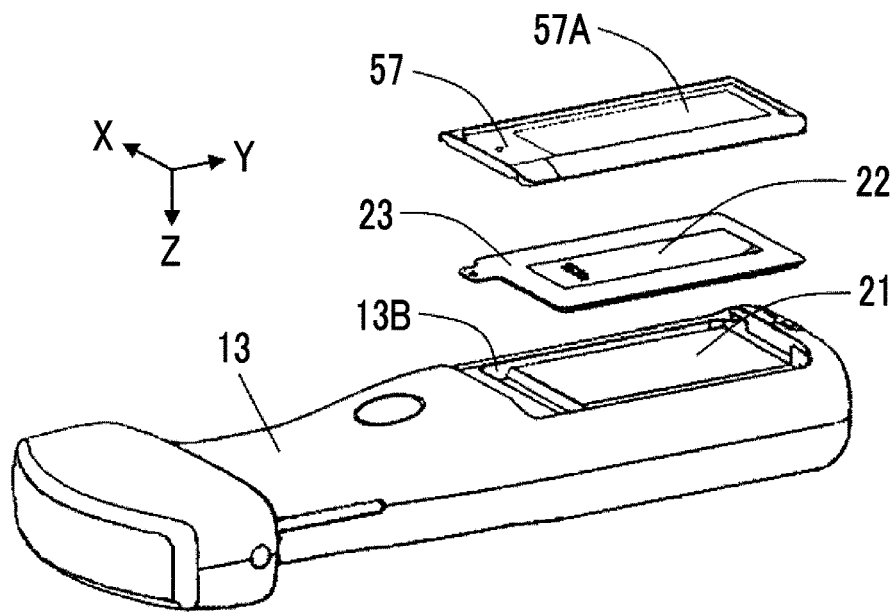
FIG. 9 is an exploded view of the periphery of a battery cover of an ultrasound probe according to a modification example of Embodiment 2 of the invention.

For example, as shown in FIG. 9, the battery cover 57 can also be attached to the grip portion 13 with the nameplate 22 and the waterproof member 23 sandwiched between the battery 21 and the battery cover 57 in a state in which the nameplate 22 is disposed on a surface on the −Z direction side of the waterproof member 23 as one of internal structure members of the battery storage portion 13B. In such a manner, the nameplate 22 is disposed on the +Z direction side of the transparent portion 57A, whereby the user can view the description of the nameplate 22 through the transparent portion 57A.

The entire surface on the −Z direction side of the nameplate 22 is covered with a transparent waterproof sheet (not shown), and a peripheral portion of the waterproof sheet is adhered to the surface on the −Z direction side of the waterproof member 23 using a waterproof double-sided tape, a waterproof adhesive, or the like, whereby a waterproof structure for restraining a liquid, such as water or a chemical, from entering the nameplate 22 from the outside is constituted.

From the above description, with the ultrasound probe according to Embodiment 2, the battery cover 57 has the transparent portion 57A, the nameplate 22 is disposed on the inside of the battery cover 57, and in particular, on the +Z direction side of the transparent portion 57A, and a liquid, such as water or a chemical, is restrained from entering the nameplate 22. Thus, as in Embodiment 1, it is possible to restrain the description of the nameplate 22 from being damaged by a chemical or the like while disposing the nameplate 22 in a state in which the description of the nameplate 22 can be viewed.

The ultrasound probe provides a waterproof rim (not shown) formed in the waterproof member 23 on the surface on the +Z direction side of the battery cover 57 to fix the battery cover 57 to the grip portion 13, instead of having the waterproof member 23, whereby it is also possible to restrain a liquid, such as water or a chemical, from entering the battery storage portion 13B. In this case, the battery cover 57 is attached to the grip portion 13 in a state in which the nameplate 22 is disposed on a surface on the −Z direction side of the battery 21 as another internal structure member of the battery storage portion 13B. In this case, the nameplate 22 is disposed on the inside of the ring-shaped waterproof rim, and thus, a liquid, such as water or a chemical, is restrained from entering the nameplate 22 from the outside.

The portion other than the transparent portion 57A of the battery cover 57 is non-transparent, but may be transparent similarly to the transparent portion 57A. Note that the portion other than the transparent portion 57A of the battery cover 57 is non-transparent, such that a portion disposed on the +Z direction side with respect to the portion battery cover 57 and positioned in the vicinity of the nameplate 22, for example, the waterproof member 23 and the like can be hidden from the outside, and thus, it is preferable that the portion other than the transparent portion 57A of the battery cover 57 is non-transparent.

EXPLANATION OF REFERENCES

1: ultrasound diagnostic apparatus
11: ultrasound probe
12: housing
13: grip portion
13A: battery storage portion
14: transducer array accommodation portion
15A, 15B: operation switch
16A, 16B, 16C: indicator
17, 57: battery cover
17A: first recess portion
17B: second recess portion
17C: hook portion
18: acoustic lens
19: transducer array
20: circuit substrate
21: battery
22: nameplate
23: waterproof member
31: transmission unit
32: reception unit
33: ultrasound transmission and reception controller
34, 42: wireless communication unit
35, 47: communication controller
36: probe controller
37: ultrasound probe-side processor
43: signal processing unit
44: image processing unit
45: display controller
46: display unit
48: body controller
49: operating unit
50: storage unit
51: diagnostic apparatus body-side processor
57A: transparent portion
C: transparent cover
H: through-hole
R: recess portion

What is claimed is:

1. An ultrasound probe comprising:
   a housing having a transducer array accommodation portion and a battery storage portion;
   a transducer array accommodated in the transducer array accommodation portion; and
   a battery stored in the battery storage portion,
   wherein the housing has an attachable and detachable battery cover that covers the battery storage portion,
   the battery cover has a recess portion formed at an outside of the battery storage portion,
   a nameplate is disposed on the recess portion, and
   a waterproof structure having a transparent cover which is attached to the battery cover so as to seal the recess portion and cover the recess portion, for restraining water from entering the nameplate is provided.

2. The ultrasound probe according to claim 1,
   wherein the transparent cover is adhered to the outer surface of the battery cover by a waterproof double-sided tape in a vicinity of the nameplate.

3. The ultrasound probe according to claim 2,
   wherein non-transparent printing is performed on a portion of the transparent cover in the vicinity of the nameplate.

\* \* \* \* \*